United States Patent [19]

Scherff

[11] 4,239,189
[45] Dec. 16, 1980

[54] HANDLING APPARATUS FOR PROBE TUBES TO BE ATTACHED TO TEMPERATURE GAGE AND/OR SAMPLING LANCES IN THE METALLURGICAL FIELD

[75] Inventor: Helmut Scherff, Neukirchen-Vluyn, Fed. Rep. of Germany

[73] Assignee: Mannesmann Demag A.G., Duisburg, Fed. Rep. of Germany

[21] Appl. No.: 71,733

[22] Filed: Aug. 31, 1979

[30] Foreign Application Priority Data

Sep. 9, 1978 [DE] Fed. Rep. of Germany ....... 2839255

[51] Int. Cl.³ ............................................. C21B 7/24
[52] U.S. Cl. ................................. 266/79; 73/DIG. 9; 73/359 R; 221/270; 266/88; 414/131; 414/754
[58] Field of Search .......................... 266/79, 88, 87; 73/DIG. 9, 359; 414/754, 131; 221/270

[56] References Cited

U.S. PATENT DOCUMENTS

| 3,650,414 | 3/1972 | Asada et al. | 414/131 |
| 3,717,034 | 2/1973 | Dukelow et al. | 73/DIG. 9 |

FOREIGN PATENT DOCUMENTS

| 2631060 | 2/1977 | Fed. Rep. of Germany | 266/79 |
| 486054 | 1/1976 | U.S.S.R. | 266/79 |

Primary Examiner—M. J. Andrews
Attorney, Agent, or Firm—Mandeville and Schweitzer

[57] ABSTRACT

A transfer and storage mechanism is provided for disposable tube probes used in metallurgy. The transfer mechanism is arranged to select from several vertical stacks of such probes and to transfer the selected probe to a lance for insertion into a converter. The same mechanism provides several functions in that it holds the selected probe tube, pivots it into position for engagement with the lance and centers the probe for engagement for the lance. Moreover, arrangements are provided for engaging and sliding the selected tube out of the storage area into the transfer mechanism.

10 Claims, 4 Drawing Figures

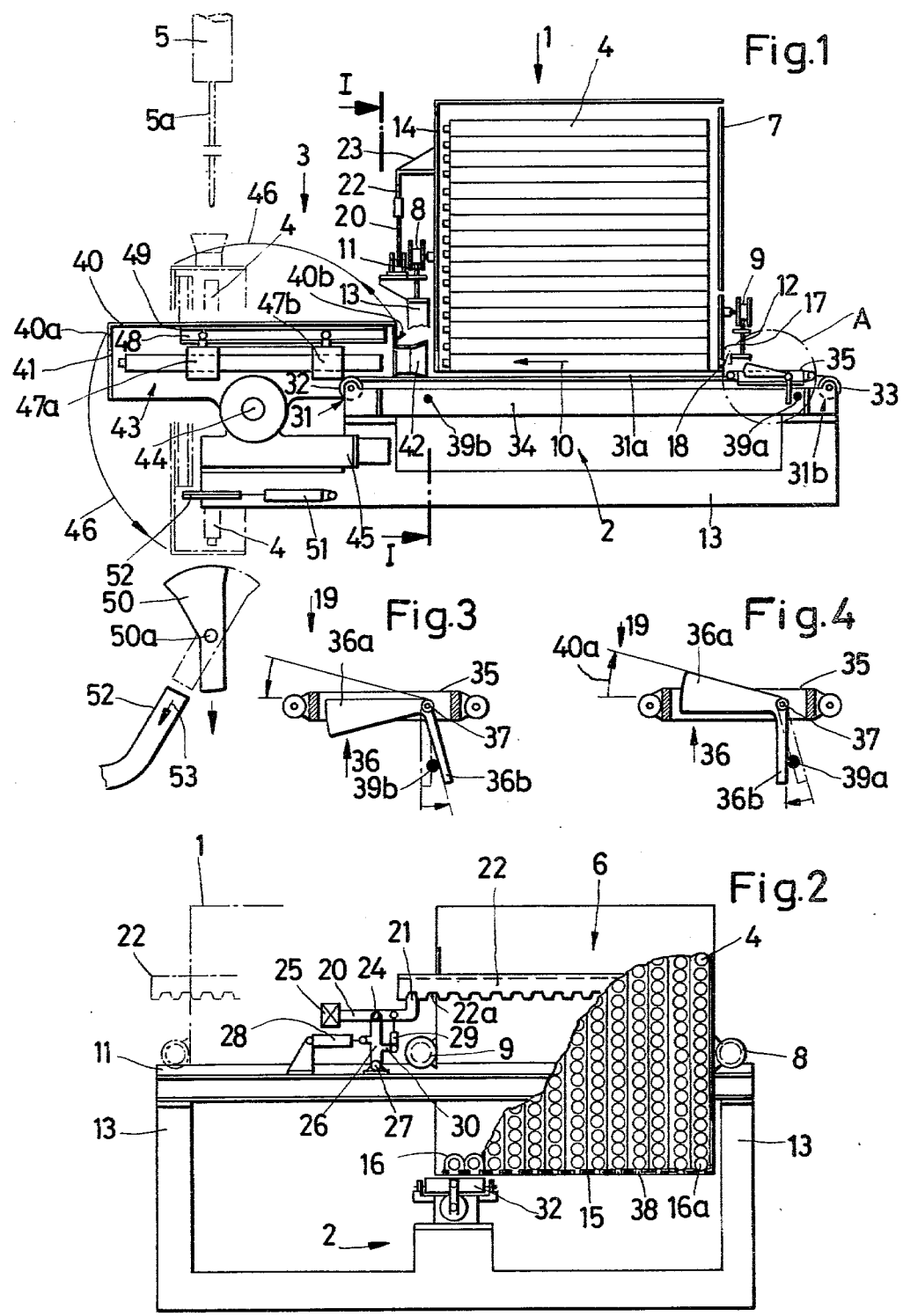

HANDLING APPARATUS FOR PROBE TUBES TO BE ATTACHED TO TEMPERATURE GAGE AND/OR SAMPLING LANCES IN THE METALLURGICAL FIELD

BACKGROUND AND DESCRIPTION OF THE INVENTION

The invention refers to handling and exchange apparatus for probe tubes to be attached to a temperature gage and/or sampling lances in the metallurgical field. The arrangement allows for pivoting of the tubes drawn from a storage tank by means of a feed mechanism, and by means of a rotatable transfer mechanism movable into a vertical transfer position, so that the support lance, with the attached probe, may be inserted into and retracted from the furnace chamber of metallurgical vessels.

Such devices serve to automate measuring and testing processes of the most diverse kinds in the manufacture of steel in metallurgical furnaces, such as in steel mill converters. The probe tubes are equipped, according to the high temperature in the metallurgical area, with test heads or sampling tools to be used only once. Probe tubes of this type are provided at one end with connecting elements which, together with corresponding connecting elements on the support lance to be raised and lowered into the furnace, facilitate a connection which can be established or released quickly. The end of the connecting element being in front, the probe tube is transported by control impulses operating the transfer apparatus remotely from the control stand of a metallurgical smelting plant.

It has been disclosed in German DE-OS No. 26 31 060 to arrange vertical rows of probe tubes of uniform diameter in a storage tank for such a supply and transfer apparatus. The apparatus is equipped with a special sampling body isolation mechanism. It consists of one support arm unit each for each vertical row of tubes, having four sections of upper and lower arms, which are arranged in pairs of two. Despite the gripping mechanism consisting of the arms, the probe tubes must be dropped via inclined sliding surfaces to the level of the feed mechanism, which is disadvantageous. Further, the disclosed supply and transfer apparatus provides a lateral arrangement of the feed device next to the storage tank which makes for a greater requirement of space. This is another disadvantage in view of the crowded conditions in a metallurgical plant. Besides the rotatable transfer device, the disclosed apparatus furthermore necessitates a special support mechanism to transfer the tubes from the feed mechanism to the support lance. This type of transport apparatus is, in its entirety, very involved and complicated.

The invention aims to simplify the known supply and transfer apparatus. Furthermore, the invention provides an apparatus for probe tubes with different cross sections, shapes and sizes. The invention provides for arranging the feed mechanism under the floor of the storage tank wherein the tubes rest on each other, forming several independent vertical rows. The invention coordinates each vertical row at the end walls of the storage tank, with a front opening matching the greatest diameter of the respective tubes, and with a rear opening for a slide; and by attaching the slide to the feed mechanism so that it aligns with the probe tube axis. Such a transport apparatus has the advantages of a simplified tube sampling mechanism, which practically consists of the feed mechanism itself, so that the feed mechanism is also arranged in a space-saving manner. Another simplification of the transfer apparatus, according to the invention, results from the omission of a special support mechanism to transfer the tubes from the feed mechanism to the support lance. A special advantage of the invention is that the storage tank may contain probe tubes of different cross sectional sizes and/or shapes.

Further, the invention is based on the concept of selecting one tube from one selected vertical row of a multitude of adjacent vertical rows. Accordingly, the invention is designed to permit horizontal movement of the storage tank or feed mechanism perpendicular to the feed direction of the feed mechanism. Also, any desired selection of tubes from the vertical rows is further facilitated by permitting movement of the storage tank or the feed mechanism.

It is also advantageous that a distribution opening is coordinated with the lowest probe tube of a vertical row. The lowest tube in the vertical row is selected and withdrawn from under the weight of the tubes being supported by each other in the vertical row. It is furthermore provided that the horizontally movable storage tank may be locked in position for withdrawing a tube.

Locating the selected vertical row of tubes is accomplished in such a manner that the locking element may be shifted back and forth by means of a drive by the distance between two vertical rows of tubes, while gripping the storage tank. The lock is cancelled by means of an additional drive. This drive may either be arranged at the front of the storage tank or beneath it, in a protected fashion.

A further improvement of the invention is the feed mechanism comprising a cable which may be moved back and forth by means of a reversible piston-cylinder drive. The rope or cable comes attached with a carrier for a dog which is mounted to project into the tubes. The carrier moves in a longitudinal direction in a guide extending along the floor of the storage tank. In the feed direction, in the starting position of the feeding movement, the carrier projects into a groove for engaging the tubes, and it is withdrawn from the groove at the starting position of the return direction of movement.

During transfer, the probe tubes are exposed to environmental conditions of the metallurgical operation. Damages to the probe tubes during transfer are avoided in accordance with further measures in that the transfer device opposite the storage tank consists of a receiver provided with a protective covering, and provided with passageways for the tubes at the end walls, such receiver being pivotal around a horizontal axis running at right angles to the tube axis, while remaining covered.

The receiver for the transfer of the tubes is, according to the invention, formed by providing under the covering at least one clamping jaw pair each for each tube. The invention further provides for a feeding movement to transfer the tube held in the receiver that the clamping jaw pairs are arranged on one common beam which is supported under the covering so as to be movable in the direction of the supported tube axis.

Provision to protect the tubes is furthermore made in that the covering surrounding the supported tube extends at least on three sides in the horizontal position, and in its vertical pivoted position affords protection from a rising exhaust gas flow, its radiation, etc. According to the present invention, the transfer device takes on the functions of clamping the tubes, swiveling and transferring them. For the transfer, it is provided that the receiver is equipped with a guide which, in vertical position of the receiver, provides a means of centering the respective probe tube in the receiver versus the opposite support lance tip.

The means for the removal of spent tubes, according to further developement of the invention, that below the receiver is a pipe switch. In the vertical normal position of the pipe switch, the spent tube, after releasing the tube clamp, drops through the pipe switch into a collecting tank placed underneath, or into the metallurgical vessel itself. In a second position of the pipe switch, a previously severed sample, as the case may be, can be dispatched to a test station for examination. For the purpose of severing the spent tube parts which are to be subjected to testing, a conventional cutting mechanism is positioned above the pipe switch to take a sample for analysis.

An example of the invention is shown on the drawing and explained as follows:

DESCRIPTION OF THE DRAWING

FIG. 1 is a side elevational view, partially in section, of apparatus illustrating the invention;

FIG. 2 is a view taken along lines I—I of FIG. 1;

FIG. 3 is an enlarged view of that portion of FIG. 1 circled by a circle designated A and showing the carrier of the feeding mechanism in inoperative position; and FIG. 4 is the same view as in FIG. 3, with the carrier in operative position.

DETAILED DESCRIPTION OF THE INVENTION

The transport apparatus comprises three main structural groups: storage tank 1, feed mechanism 2, transfer mechanism 3. The tubes 4, to be transported, are to be attached to support lance 5 and/or 5a depending on their temperature gage and/or sampling functions. The area laterally below the support lance 5 contains a converter or other metallurgical vessel which is not shown in detail. The storage tank 1 contains rows 6 of vertically supported tubes 4 whose functions and cross sections may differ from row to row.

The probe tubes 4 are brought into the storage tank through a door 7. With only one single feed mechanism 2, the storage tank 1 is displaceable, by means of wheel pairs 8 and 9 affixed to it, horizontally on rails 11 and 12 running perpendicular to the feeding direction 10. The rails are supported on frame 13, carrying the entire transport apparatus. At the left end wall 14 at a row of 6 probe tubes 4, distribution openings 16 are provided in the area of the floor 15, and rear openings 18 for the slide 19 shown in FIGS. 3 and 4 are provided in the right end wall 17. This is a portion of the feed mechanism 2. The back-and-forth movement of the storage tank 1 is caused by a lever 20 whose tip is designed as a tooth 21 engaging the rack 22, the latter being attached to the storage tank 1 by means of a bracket 23. While engaged, the lever 20 (as shown in FIG. 2) simultaneously forms a locking element to retain the storage tank 1 at the moment of feeding one probe tube 4, and to avoid any undesirable lateral movement as well as to guarantee, simultaneously, a centered engagement of the slide 19 with the probe tube. The lever 20 pivots around axis 24, provided with the balancing weight 25, and hinged to the roughly vertically positioned intermediate link 26. The latter pivots around horizontal axis 27, which is fixed to frame 13 next to the rail 11. A first piston-cylinder 28 is hinged to intermediate link 26 including the pivotal movements of intermediate link 26.

Piston-cylinder 28 is attached to frame 13. A second piston cylinder gear 29, hinged on lever 20 and on arm 30 of intermediate link 26, pivots lever 20 relative to the rack 22, for locking purposes on one hand, as shown in FIG. 2, or to advance the storage tank 1 by the width of the distance between two vertical rows 6 by engagement with the next gap between teeth 22a. The distance from row 6 to row 6, therefore, matches the division of the rack 22. In the outermost position shown in dot-dash lines of the storage tank in FIG. 2, the last distribution opening 16a is aligned with the feed mechanism 2.

The feed mechanism 2 has a drive chain or rope 31 extending over pulleys 32 and 33 attached to frame 13. The slide 19 is attached to the upper run of drive chain 31. The ends of rope or chain 31 at the lower run 31b are attached to a double acting piston-cylinder gear 34 for moving the slide 19 in a feeding return movement.

Slide 19 consists of a carrier beam 35 (FIGS. 3 and 4) attached to the end of drive 31. The carrier 36 pivots in the carrier beam 35 around pivot 37, and consists of an angle lever with arms 36a, 36b. The carrier slides in one slotted guide 38 provided in the floor 15 of the storage tank 1 below each row 6 of vertically stacked probe tubes 4.

In order to feed or advance a probe tube 4, the arm 36a is pivoted by pushing the arm 36b, in the direction of arrow 40a, against the stop 39a into the position, as shown in FIG. 4, and protruding beyond the carrier beam 35. At the same time the arm 36a enters the slot guide 38. This process takes place in the last part of the return movement. In the last part of the feeding movement, the arm 36b pushes against the stop 36b and pivots the arm 36a into the carrier beam 35, as shown in FIG. 3. During the return movement, the arm 36a remains in the lowered position. In this position, there is also no sliding within the slotted guide 38. The higher stored tubes 4 slowly slide down during the feeding movement.

The transfer mechanism has a covering 40 protecting in horizontal and in vertical position the parts underneath. This covering extends over the end walls 40a, 40b. The latter are provided with openings 41 as well as another opening 42, designed as a funnel, through which the tube 4 to be transported is inserted. The receiver 43 is attached to the covering 40, and is rotatable in the perpendicular plane by means of the horizontal pivot axis 44. The rotary gear 45 is also provided in a protected location underneath covering 40. The vertical position, shown in dot-dash lines in FIG. 1, is achieved by pivoting the transfer mechanism 3 in the direction of the arrow 46.

The covering 40 is further provided with a clamping jaw pair 47a, 47b. The latter is supported on common beam 48, which is displaceable in a guide 49, parallel with the probe tube 4. Of particular advantage is the fact that by pivoting the transfer mechanism 3, the opening 42 formed as a funnel serves as a means of centering the support lance 5. The latter is lowered into the funnel, and then a conventional plug coupling makes the connection between the support lance 5 and the tube 4.

After the test procedure in the metallurgical vessel, where the test data are transmitted via electric lines within the support lance 5 and/or 5a within a short time, and after the support lance 5 with its part 5a has been retracted from the metallurgical vessel, the burnt probe tube 4 remains merely as residue on the support lance part 5a. Upon disengaging, this remainder drops through the pipe switch 50 which is in the vertical position as drawn, into a container or into the metallurgical vessel proper. In case of sampling the smelt in the metallurgical vessel, it is severed by means of the blade 52 in the cutting mechanism 51 and the pipe switch 50 is pivoted into the position indicated in dot-dash lines in FIG. 1 around axis 50a so that the sample for analysis goes through the pipe 52, for example, by means of compressed air, in the direction of the arrow 53 directly to the laboratory.

I claim:

1. Apparatus for transferring probe tubes, to be attached to a temperature gage or sampling lance in metallurgical operations, comprising
   (a) a storage tank for a plurality of probe tubes;
   (b) a transfer mechanism for receiving a selected probe from said storage tank and moving it to a position for engagement with a lance or gage;
   (c) a feed mechanism for selecting and moving a probe tube from said storage tank to said transfer mechanism;
   (d) said transfer mechanism rotatable from a horizontal receiving position to a vertical feeding position for said probe tubes; the improvement characterized by
   (e) a plurality of vertically stacked probe tubes positioned in said storage tank;
   (f) an opening in the front wall of said storage tank adjacent the bottom row of each stack of probe tubes;
   (g) said probe tubes movable out of said front opening into said transfer mechanism;
   (h) an opening in the rear walls of said storage tank, adjacent the bottom row of each stack of probe tubes; and
   (i) said feed mechanism extending through said rear openings to engage and feed selected ones of said probe tubes to said transfer mechanism.

2. The apparatus of claim 1, further characterized by
   (a) said storage tank and said feed mechanism are movable horizontally relative to each other to engage a selected one of said front openings and rear openings to said feed mechanism and said transfer mechanism; and
   (b) said relative movement is perpendicular to the feed movement of said feed mechanism.

3. The apparatus of claim 2, further characterized by
   (a) said storage tank includes means for locking said tank in a feed position for one of said tubes to be fed.

4. The apparatus of claim 3, further characterized by said locking means includes
   (a) a rack;
   (b) a locking detent for selectively engaging said rack;
   (c) first reversible pressure fluid means connected to said detent for selectively engaging said detent; and
   (d) second reversible fluid pressure means connected to said detent for removing said locking detent from engagement with said rack.

5. The apparatus of claim 1, further characterized by said feeding mechanism including
   (a) a drive chain;
   (b) a reversible pressure fluid cylinder connecting each end of said drive chain;
   (c) a carrier connected to said drive chain;
   (d) engaging means on said carrier for extending into said rear openings for engaging said probe tubes; and
   (e) a plurality of spaced longitudinal grooves in the bottom surface of said storage tank for receiving said engaging means.

6. The apparatus of claim 5, further characterized by
   (a) said engaging means engages the selected probe tube in the starting position of the feeding movement of said carrier; and
   (b) said engaging means moves out of engagement with said probe tubes at the starting position of the return movement of said carrier.

7. The apparatus of claim 1, further characterized by said transfer mechanism including
   (a) a cover plate extending over each end wall of said transfer mechanism;
   (b) an opening in said cover in each end wall for receiving said probe tubes; and
   (c) at least one clamping jaw in said transfer means for engaging a probe tube therein.

8. The apparatus of claim 7, further characterized by
   (a) a pair of clamping jaws for engaging a probe tube therein; and
   (b) a longitudinally movable support beam for said jaws;
   (c) said support beam movable parallel to the axis of a probe tube therein.

9. The apparatus of claim 8, further characterized by
   (a) a funnel shaped guide in one said transfer mechanism opening; and
   (b) said guide forming a centering piece for engagement of said probe tube in the vertical feeding position thereof by a support lance tip.

10. The apparatus of claim 1, further characterized by
   (a) a pipe switch positioned below said transfer mechanism;
   (b) said pipe switch providing a continuing path for said probe tube in the vertical position thereof;
   (c) a cutter positioned above said pipe switch for severing a test sample of a used probe tube; and
   (d) said pipe switch rotatable into different positions for directing said severed test sample into the proper channel.

* * * * *